US010828476B2

(12) United States Patent
Juravic

(10) Patent No.: US 10,828,476 B2
(45) Date of Patent: Nov. 10, 2020

(54) SYSTEMS AND METHODS FOR THE TREATMENT AND PREVENTION OF FEMALE PELVIC DYSFUNCTION

(71) Applicant: MATERNA MEDICAL, INC., Mountain View, CA (US)

(72) Inventor: Mark Juravic, San Francisco, CA (US)

(73) Assignee: MATERNA MEDICAL, INC., Mountain View, CA (US)

( * ) Notice: Subject to any disclaimer, the term of this patent is extended or adjusted under 35 U.S.C. 154(b) by 147 days.

(21) Appl. No.: 15/741,774

(22) PCT Filed: Jul. 11, 2016

(86) PCT No.: PCT/US2016/041749
§ 371 (c)(1),
(2) Date: Jan. 4, 2018

(87) PCT Pub. No.: WO2017/011389
PCT Pub. Date: Jan. 19, 2017

(65) Prior Publication Data
US 2018/0193619 A1 Jul. 12, 2018

Related U.S. Application Data

(60) Provisional application No. 62/190,995, filed on Jul. 10, 2015.

(51) Int. Cl.
*A61M 29/02* (2006.01)
*A61M 29/00* (2006.01)
(Continued)

(52) U.S. Cl.
CPC ............ *A61M 29/00* (2013.01); *A61B 17/42* (2013.01); *A61D 1/10* (2013.01); *A61M 29/02* (2013.01);
(Continued)

(58) Field of Classification Search
CPC ....... A61M 29/00; A61M 29/02; A61B 17/42; A61B 17/00557; A61B 17/22032;
(Continued)

(56) References Cited

U.S. PATENT DOCUMENTS

| 237,032 A | 1/1881 | Mayer |
| 242,443 A | 6/1881 | Foote |

(Continued)

FOREIGN PATENT DOCUMENTS

| CN | 2262410 Y | 9/1997 |
| CN | 2555047 Y | 6/2003 |

(Continued)

OTHER PUBLICATIONS

Hofmeyr et al.; An inflatable birth canal dilator; SAMJ; vol. 80; pp. 198-199; Aug. 17, 1991.

(Continued)

*Primary Examiner* — Vi X Nguyen
(74) *Attorney, Agent, or Firm* — Shay Glenn LLP

(57) ABSTRACT

Systems for the treatment and prevention of pelvic dysfunction are provided. In one embodiment, a vaginal dilation device includes a handle portion and a shaft portion. The shaft portion is configured to expand from a collapsed configuration to an expanded configuration. The shaft portion can include a distal tip region, a spine region, and a distal arm region connecting the distal tip region to the spine region. The spine region can extend distally from the handle portion to the distal arm region, and can be generally tubular in shape. The distal arm region can be generally conical in shape and be configured to provide a gradual increase in diameter from the distal tip region to the spine region. Methods of use are also provided.

13 Claims, 4 Drawing Sheets

(51) Int. Cl.
*A61B 17/42* (2006.01)
*A61D 1/10* (2006.01)
A61B 17/00 (2006.01)
A61B 90/00 (2016.01)

(52) U.S. Cl.
CPC .............. *A61B 2017/00022* (2013.01); *A61B 2017/00199* (2013.01); *A61B 2017/00398* (2013.01); *A61B 2090/061* (2016.02); *A61M 2205/8237* (2013.01); *A61M 2210/1475* (2013.01)

(58) Field of Classification Search
CPC .... A61B 2017/00398; A61B 17/12136; A61B 17/12099
See application file for complete search history.

(56) References Cited

U.S. PATENT DOCUMENTS

| | | |
|---|---|---|
| 275,405 A | 4/1883 | Parker |
| 292,381 A | 1/1884 | Stiles |
| 316,611 A | 4/1885 | Farr |
| 318,535 A | 5/1885 | Bihler |
| 365,969 A | 7/1887 | Collins |
| 376,727 A | 1/1888 | Beall |
| 458,022 A | 8/1891 | Jeanjaquet |
| 458,457 A | 8/1891 | Hendrickson |
| 468,620 A | 2/1892 | Hitt |
| 540,835 A | 6/1895 | Gunning |
| 577,775 A | 2/1897 | Mussey |
| 705,371 A | 7/1902 | Anderson et al. |
| 837,085 A | 11/1906 | Loar |
| 899,477 A | 9/1908 | Williams |
| 923,303 A | 6/1909 | Shults |
| 972,983 A | 12/1909 | Arthur |
| 1,034,818 A | 8/1912 | Mulgrew |
| 1,076,221 A | 12/1912 | Miner |
| 1,244,751 A | 10/1917 | McCleary |
| 1,271,456 A | 7/1918 | Flack |
| 1,382,982 A | 6/1921 | Jeanjaquet |
| 1,413,789 A | 4/1922 | Van Schaff |
| 1,428,653 A | 9/1922 | Nick |
| 1,448,158 A | 3/1923 | Sims |
| 1,528,858 A | 3/1925 | Sims |
| 1,582,690 A | 4/1926 | Reggio |
| 1,737,488 A | 11/1929 | Zohlen |
| 1,764,838 A | 6/1930 | Home |
| 1,827,497 A | 10/1931 | Thomas |
| 2,026,747 A | 1/1936 | Nemzek |
| 2,083,573 A | 6/1937 | Morgan |
| 2,137,121 A | 11/1938 | Fannie |
| 2,507,858 A | 5/1950 | Kegel |
| 2,541,520 A | 2/1951 | Kegel |
| 2,610,626 A | 9/1952 | Edwards |
| 2,849,001 A | 8/1958 | Oddo |
| 2,849,002 A | 8/1958 | Oddo |
| 3,039,462 A | 6/1962 | Walden et al. |
| 3,045,677 A | 7/1962 | Wallace |
| 3,192,928 A | 7/1965 | Horton |
| 3,480,017 A | 11/1969 | Shute |
| 3,502,328 A | 3/1970 | Hamilton |
| 3,517,128 A | 6/1970 | Hines |
| 3,532,088 A | 10/1970 | Fiore |
| 3,565,061 A | 2/1971 | Reynolds |
| 3,626,949 A | 12/1971 | Shute |
| 3,769,968 A | 11/1973 | Blount et al. |
| 3,799,170 A | 3/1974 | Walsh et al. |
| 3,841,318 A | 10/1974 | Olso |
| 3,916,906 A | 11/1975 | Gerry |
| 3,968,800 A | 7/1976 | Vilasi |
| 4,018,231 A | 4/1977 | Wallace |
| 4,050,449 A | 9/1977 | Castellana et al. |
| 4,130,113 A | 12/1978 | Graham |
| 4,167,938 A | 9/1979 | Remih |
| 4,198,981 A | 4/1980 | Sinnreich |
| 4,241,912 A | 12/1980 | Mercer et al. |
| 4,306,459 A | 12/1981 | Johnson et al. |
| 4,396,019 A | 8/1983 | Perry |
| 4,476,880 A | 10/1984 | Giem et al. |
| 4,515,167 A | 5/1985 | Hochman |
| 4,566,465 A | 1/1986 | Arhan et al. |
| 4,653,514 A | 3/1987 | Shapiro |
| 4,664,114 A | 5/1987 | Ghodsian |
| 4,677,967 A | 7/1987 | Zartman |
| 4,749,186 A | 6/1988 | Harding Randle |
| 4,753,238 A | 6/1988 | Gaiser |
| 4,768,522 A | 9/1988 | Shapiro |
| 4,785,828 A | 11/1988 | Maurer |
| 4,832,691 A | 5/1989 | Witzel |
| 4,875,482 A | 10/1989 | Hariri et al. |
| 4,884,559 A | 12/1989 | Collins |
| 4,971,036 A | 11/1990 | Collins |
| 5,072,720 A | 12/1991 | Francis et al. |
| 5,081,983 A | 1/1992 | Villalta et al. |
| 5,147,377 A | 9/1992 | Sahota |
| 5,179,937 A | 1/1993 | Lee |
| 5,209,754 A | 5/1993 | Ahluwalia |
| 5,231,973 A | 8/1993 | Dickie |
| 5,275,610 A | 1/1994 | Eberbach |
| 5,338,297 A | 8/1994 | Kocur et al. |
| 5,354,250 A | 10/1994 | Christensen |
| 5,377,667 A | 1/1995 | Patton et al. |
| 5,465,709 A | 11/1995 | Dickie et al. |
| 5,483,832 A | 1/1996 | Pauser et al. |
| 5,509,893 A | 4/1996 | Pracas |
| 5,674,238 A | 10/1997 | Sample et al. |
| 5,681,340 A | 10/1997 | Veronikis |
| 5,733,230 A | 3/1998 | Sawchuck et al. |
| 5,743,852 A | 4/1998 | Johnson |
| 5,746,750 A | 5/1998 | Prestel et al. |
| 5,762,589 A | 6/1998 | Parker, Jr. |
| 5,795,289 A | 8/1998 | Wyttenbach |
| 5,865,715 A | 2/1999 | Wallick |
| 5,876,357 A | 3/1999 | Tomer |
| 5,916,151 A | 6/1999 | Charters |
| 5,947,991 A | 9/1999 | Cowan |
| 6,024,696 A | 2/2000 | Hoftman et al. |
| 6,024,697 A | 2/2000 | Pisarik |
| 6,027,519 A | 2/2000 | Stanford |
| 6,048,308 A | 4/2000 | Strong |
| 6,059,740 A | 5/2000 | Leivseth et al. |
| 6,063,045 A | 5/2000 | Wax et al. |
| 6,068,581 A | 5/2000 | Anderson |
| D428,631 S | 7/2000 | Stein |
| 6,086,549 A | 7/2000 | Neese et al. |
| 6,096,046 A | 8/2000 | Weiss |
| 6,159,170 A | 12/2000 | Borodulin et al. |
| 6,224,525 B1 | 5/2001 | Stein |
| 6,224,580 B1 | 5/2001 | Christensen |
| 6,258,015 B1 | 7/2001 | Blackford et al. |
| D446,856 S | 8/2001 | Stein |
| D446,857 S | 8/2001 | Stein |
| D447,234 S | 8/2001 | Stein |
| D447,235 S | 8/2001 | Stein |
| D447,236 S | 8/2001 | Stein |
| 6,280,379 B1 | 8/2001 | Resnick |
| D447,562 S | 9/2001 | Stein |
| D447,563 S | 9/2001 | Stein |
| D447,800 S | 9/2001 | Stein |
| D448,080 S | 9/2001 | Moscarelli et al. |
| 6,302,842 B1 | 10/2001 | Auerbach et al. |
| 6,342,036 B1 | 1/2002 | Cooper et al. |
| 6,354,995 B1 | 3/2002 | Hoftman et al. |
| 6,402,683 B1 | 6/2002 | Marty |
| 6,468,232 B1 | 10/2002 | Ashton Miller et al. |
| 6,540,667 B2 | 4/2003 | Hickman |
| 6,672,996 B2 | 1/2004 | Ross et al. |
| 6,688,310 B1 | 2/2004 | Toliver |
| 6,749,563 B2 | 6/2004 | Stihl |
| 6,752,749 B2 | 6/2004 | Stein |
| 6,758,796 B2 | 7/2004 | Stein |
| 6,773,380 B2 | 8/2004 | Stein |
| 6,843,251 B1 | 1/2005 | Huerland et al. |

(56) References Cited

U.S. PATENT DOCUMENTS

| | | |
|---|---|---|
| 6,869,398 B2 | 3/2005 | Obenchain et al. |
| 6,905,471 B2 | 6/2005 | Leivseth et al. |
| 6,932,764 B2 | 8/2005 | Kashyap |
| 7,001,317 B2 | 2/2006 | Marcotte |
| 7,014,603 B2 | 3/2006 | Stein |
| 7,060,029 B1 | 6/2006 | Hajianpour |
| 7,141,015 B2 | 11/2006 | Ruane |
| 7,182,730 B2 | 2/2007 | Fehling |
| 7,322,935 B2 | 1/2008 | Palmer et al. |
| 7,481,766 B2 | 1/2009 | Lee et al. |
| 7,497,816 B2 | 3/2009 | Li |
| 7,577,476 B2 | 8/2009 | Hochman et al. |
| 7,628,744 B2 | 12/2009 | Hoffman et al. |
| 7,645,220 B2 | 1/2010 | Hoffman et al. |
| 7,713,216 B2 | 5/2010 | Dubey et al. |
| 7,771,344 B2 | 8/2010 | Ziv |
| 8,097,014 B2 | 1/2012 | Borkon |
| 8,118,726 B1 | 2/2012 | Blackford |
| 8,187,208 B2 | 5/2012 | Egorov et al. |
| 8,876,711 B2 | 11/2014 | Lin et al. |
| 9,492,197 B2 | 11/2016 | Juravic et al. |
| 2001/0041874 A1 | 11/2001 | Reydel |
| 2002/0010441 A1 | 1/2002 | Horkel |
| 2002/0016528 A1 | 2/2002 | Tan |
| 2002/0068900 A1 | 6/2002 | Barnes et al. |
| 2002/0095160 A1 | 7/2002 | Bonutti |
| 2003/0036464 A1 | 2/2003 | Zavilevich |
| 2003/0069476 A1 | 4/2003 | Deslauriers et al. |
| 2003/0078526 A1 | 4/2003 | Farley |
| 2003/0087734 A1 | 5/2003 | Kring et al. |
| 2003/0105387 A1 | 6/2003 | Frumovitz et al. |
| 2004/0038783 A1 | 2/2004 | Hunter |
| 2004/0153116 A1 | 8/2004 | Nobles et al. |
| 2004/0225235 A1 | 11/2004 | Ben-Cnaan et al. |
| 2005/0049509 A1 | 3/2005 | Mansour et al. |
| 2005/0148447 A1 | 7/2005 | Nady |
| 2005/0154263 A1 | 7/2005 | Nady |
| 2005/0250993 A1 | 11/2005 | Jaeger |
| 2006/0058831 A1 | 3/2006 | Atad |
| 2006/0200187 A1 | 9/2006 | Gude |
| 2007/0043264 A1 | 2/2007 | Gillis et al. |
| 2007/0043388 A1 | 2/2007 | Greenwood |
| 2007/0156068 A1 | 7/2007 | Dubey et al. |
| 2008/0039865 A1 | 2/2008 | Shaher et al. |
| 2008/0058604 A1 | 3/2008 | Sorensen |
| 2008/0139876 A1 | 6/2008 | Kim |
| 2008/0234719 A1 | 9/2008 | Adams |
| 2008/0249534 A1 | 10/2008 | Gruber et al. |
| 2009/0012556 A1 | 1/2009 | Boudreaux et al. |
| 2009/0099422 A1 | 4/2009 | George |
| 2010/0048977 A1 | 2/2010 | Sing et al. |
| 2010/0048978 A1 | 2/2010 | Sing et al. |
| 2010/0113939 A1 | 5/2010 | Mashimo et al. |
| 2010/0160947 A1 | 6/2010 | Akyuz et al. |
| 2010/0174148 A1 | 7/2010 | Miles et al. |
| 2010/0185123 A1 | 7/2010 | Zanetti et al. |
| 2010/0217088 A1 | 8/2010 | Heiges et al. |
| 2010/0217090 A1 | 8/2010 | Heiges et al. |
| 2010/0274159 A1 | 10/2010 | Perle et al. |
| 2010/0305406 A1 | 12/2010 | Braun et al. |
| 2011/0034776 A1 | 2/2011 | Dixon et al. |
| 2013/0018408 A1 | 1/2013 | Farley |
| 2013/0144388 A1 | 6/2013 | Emery et al. |
| 2013/0253376 A1* | 9/2013 | Juravic ............... A61B 17/42 600/588 |
| 2016/0166282 A1 | 6/2016 | Juravic et al. |
| 2017/0056069 A1 | 3/2017 | Juravic et al. |

FOREIGN PATENT DOCUMENTS

| | | |
|---|---|---|
| CN | 203424920 U | 2/2014 |
| CN | 204364536 U | 6/2015 |
| DE | 3803727 C1 | 4/1989 |
| DE | 3800744 C1 | 5/1989 |
| EP | 663197 B1 | 7/1995 |
| EP | 0574966 B1 | 3/1996 |
| EP | 1600103 A1 | 11/2005 |
| EP | 2229884 A1 | 9/2010 |
| FR | 592104 | 7/1925 |
| FR | 2071338 | 9/1971 |
| GB | 15314 A | 8/1903 |
| GB | 2297036 A | 7/1996 |
| JP | H10-305042 A | 11/1998 |
| JP | 2005287989 A | 10/2005 |
| KR | 1992-0021172 | 12/1992 |
| KR | 2000-0011380 | 7/2000 |
| RU | 2071285 C1 | 1/1997 |
| WO | WO98/09565 A1 | 3/1998 |
| WO | WO98/42400 A1 | 10/1998 |
| WO | WO00/12832 A2 | 3/2000 |
| WO | WO01/10493 A1 | 2/2001 |
| WO | WO01/41627 A2 | 6/2001 |
| WO | WO01/68181 A1 | 9/2001 |
| WO | WO2004/062489 A1 | 7/2004 |
| WO | WO2005/037361 A2 | 4/2005 |
| WO | WO2009/000056 A2 | 12/2008 |
| WO | WO2009/110863 A1 | 9/2009 |
| WO | WO2009/158435 A1 | 12/2009 |
| WO | WO2010/076555 A1 | 7/2010 |
| WO | WO2010/080497 A2 | 7/2010 |
| WO | WO2011/064774 A1 | 6/2011 |

OTHER PUBLICATIONS

Lee et al.; Cervetics (Business Proposal) Dila-Pro: A smart cervical dilation device; pp. 1-10; Dec. 14, 2009.

Lee et al.; Cervetics (Design Summary) Dila-Pro: A smart cervical dilation device; pp. 1-48; Dec. 14, 2009.

* cited by examiner

SYSTEMS AND METHODS FOR THE TREATMENT AND PREVENTION OF FEMALE PELVIC DYSFUNCTION

CROSS REFERENCE TO RELATED APPLICATIONS

This application claims the benefit of priority of U.S. Provisional Appln. No. 62/190,995, filed Jul. 10, 2015, the disclosure of which is incorporated by reference herein.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD

Devices and methods are described generally relating to preparing tissue for childbirth. Devices and methods are described generally to treating patients suffering from pelvic pain. More specifically, these devices are design to provide dilation physical therapy to patients undergoing treatment for pelvic pain.

BACKGROUND

There are several conditions that can lead to chronic pelvic pain. One example is a condition called Vaginismus, which is a physical and/or physiological condition in which pelvic muscles are chronically contracted, which can lead to constant pain and discomfort. The condition can cause involuntary tightness of the vagina during intercourse, caused by contractions of the pelvic floor muscles surrounding the vagina. Vaginismus can be painful, thereby affecting a women's ability to engage in any form of vaginal penetration, including sexual intercourse and insertion of tampons. There are several other primary conditions that can cause pelvic pain that eventually lead to hypertonic pelvic muscle contractions It is estimated that approximately several hundred thousand women seek treatment for pelvic pain in the United States every year. The current treatment for vaginismus involves the use of vaginal dilators of increasing size to stretch the pelvic muscles and train the muscles to relax. These vaginal dilator kits typically include several dilators of varying sizes, typically 5-8 individual dilators. Users insert the dilators into the vagina, typically starting with the smallest diameter dilator, and slowly work up to larger diameter dilators as they become comfortable with each insertion. Currently, the average patient uses dilators for over 6 months before becoming comfortable with their largest target diameter. Vaginal dilators combined with appropriate exercises have helped some women overcome these involuntary muscle contractions. However, traditional dilator sets are cumbersome and bulky to use and store, requiring multiple dilators of differing sizes.

SUMMARY OF THE DISCLOSURE

A vaginal dilation device adapted to expand from a collapsed configuration to an expanded configuration, comprising a handle portion, a shaft portion extending distally from the handle portion to a distal tip, the handle portion comprising a distal tip region disposed at the distal tip of the shaft portion, the distal tip region configured to maintain a constant diameter profile in both the collapsed configuration and the expanded configuration, a spine region extending distally from a proximal end of the shaft portion, the spine region being generally tubular in shape and being configured to expand in diameter as the shaft portion expands from the collapsed configuration to the expanded configuration, and a distal arm region connecting the distal tip region to the spine region, the distal arm region being generally conical in shape and being configured to provide a gradual increase in diameter along the shaft portion from the distal tip region to the spine region.

In one embodiment, the device comprises a diameter sensor configured to measure a diameter of the spine region. In another embodiment, the device further comprising a diameter gauge configured to display the diameter of the spine region to a user of the device.

In one embodiment, the device comprises a central rod that extends along a length of the shaft portion into the handle portion. The device can further comprise a motor coupled to the central rod, wherein operation of the motor causes the shaft portion to expand from the collapsed configuration into the expanded configuration.

In some embodiments, the device comprises a first hub and a second hub, the first hub being fixed relative to the motor, and the second hub being configured to move along the central rod when the motor is operated to expand the spine region and distal arm region.

In some embodiments, the spine region comprises a plurality of spines arranged parallel to each other. In another embodiment, the distal arm region comprises a plurality of distal arms that connect the distal tip to the plurality of spines.

In one embodiment, the device comprises a plurality of arms that connect the first hub to the plurality of spines, and further comprising a plurality of arms that connect the second hub to the plurality of spines.

In some embodiments, a diameter of the spine region in the collapsed configuration is less than 1.5 cm. In other embodiments, a diameter of the spine region in the expanded configuration is approximately 2-4 cm.

In one embodiment, the device comprises an expansion button disposed on the handle portion, the expansion button being configured to incrementally increase a diameter of the spine region when actuated by a user of the device. In some embodiments, the diameter is incrementally increased by 1 mm with each actuation of the expansion button. In other embodiments, the diameter is incrementally increased by less than 1 cm with each actuation of the expansion button.

In another embodiment, the device further comprises a vibrating element disposed in the shaft portion.

A vaginal dilation device adapted to expand from a collapsed configuration to an expanded configuration is provided, comprising a handle portion, a motor disposed within the handle portion, a central rod coupled to the motor and extending distally from the handle portion towards a distal tip, a first hub through which the central rod is configured to pass, the first hub being fixed relative to the motor, a second hub through which the central rod is configured to pass, the second hub being configured to move along the central rod when the motor is operated, a first plurality of arms connecting the first hub to a plurality of spines, a second plurality of arms connecting the second hub to the plurality of spines, a plurality of distal arms connecting the distal tip to the plurality of spines, wherein operation of the motor causes the second hub to move along the central rod, which increases an angle of the first and second plurality of arms to increase relative to the central rod, which causes the plurality of spines to extend radially away from the central rod such that the plurality of the spines remain substantially parallel to each other.

In one embodiment, a diameter of the plurality of spines in the collapsed configuration is less than 1.5 cm. In another embodiment, a diameter of the plurality of spines in the expanded configuration is approximately 2-4 cm.

In some embodiments, a diameter of the plurality of spines is incrementally controllable by a user.

In one embodiment, the device further comprises a diameter sensor configured to measure a diameter of the spine region. The device can further comprise a diameter gauge configured to display the diameter of the spine region to a user of the device.

In another embodiment, the device further comprises a vibrating element disposed near the distal tip.

A method of dilating a female's vagina, comprising the steps of inserting a vaginal dilation device into the female's vagina, incrementally expanding the vaginal dilation device with an expansion mechanism of the vaginal dilation device to dilate the female's vagina to treat vaginismus.

DETAILED DESCRIPTION

The devices and methods described herein are intended to prepare and dilate vaginal tissue to stretch the muscles of the pelvic floor and train the pelvic muscles to relax. The devices and methods described herein can be used to overcome the physical and/or physiological conditions that cause vaginismus, or involuntary tightness or contractions of the pelvic muscles in women. Expansion of the devices described herein can be controlled either manually by the user or with an automatic expansion mechanism. The devices described herein can include additional features, including force and/or diameter sensors, vibration features, and data logging features to track the usage of the device.

The devices described herein can include an expandable vaginal dilator configured to treat vaginismus. The expandable vaginal dilator is a single device that can replace a set of dilators of different sizes that is commonly used to treat vaginismus. In some embodiments, the devices described herein includes a shaft portion with an expandable portion that increases in diameter and a tip portion that maintains a constant profile and does not expand while the expandable portion is expanded.

The devices described herein can include features that increase the ease of use, including an expandable cover to seal the device and enable easy cleaning, and a charging dock or case configured to charge a battery of the device.

Figure 1A:
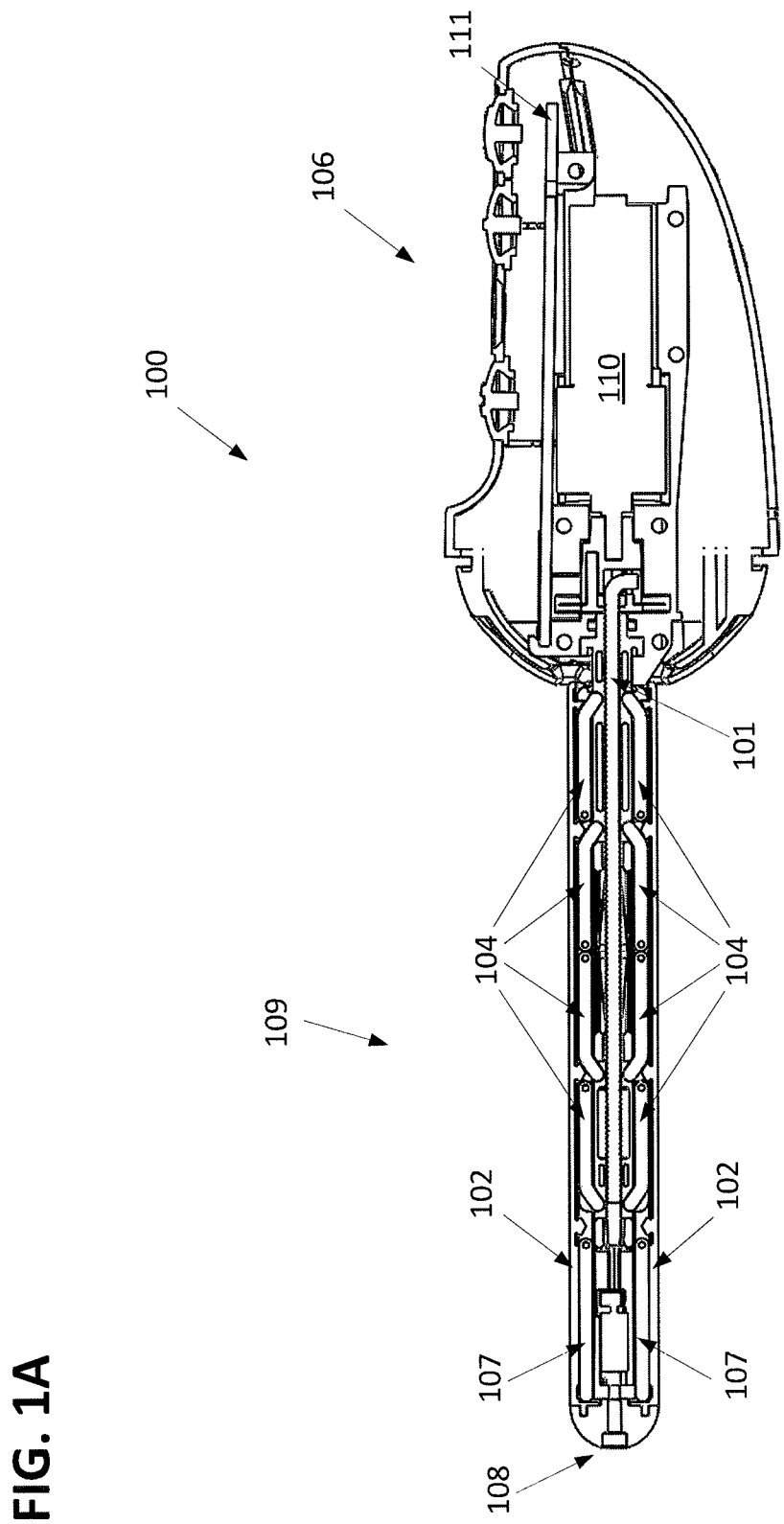
FIGS. 1A-1C show one embodiment of a vaginal dilation device.

FIG. 1A illustrates a cross-sectional view a vaginal dilation device 100 in a closed or compact configuration. Vaginal dilation device 100 can include, among other features, a central rod 101, spines 102, arms 104, a handle or frame 106, distal arms 107, distal tip 108, a shaft portion 109, a motor 110, and electronic controller 111. The shaft portion generally comprises the portion of the device that extends along the central rod, spines, distal arms, and distal tip (e.g., the portion of the device distal to the handle or frame). The motor 110 can be coupled to the central rod 101 and configured to expand the spines 102 and arms 104 radially outwards from the central rod. The motor 110 can be a rotational motor. In some embodiments, the central rod 101 is directly connected to the motor 110, and in other embodiments, the central rod 101 can be mechanically coupled to the motor via a separate coupling device. For example, in FIG. 1A, the proximal end of the central rod 101 can be bent into a coupling device which is connected to the rotating shaft of the motor. In either approach, one full rotation of the motor results in one full rotation of the central rod 101. Power to the device can be provided via a battery within the handle, or by being plugged directly into a power outlet.

Figure 1B:
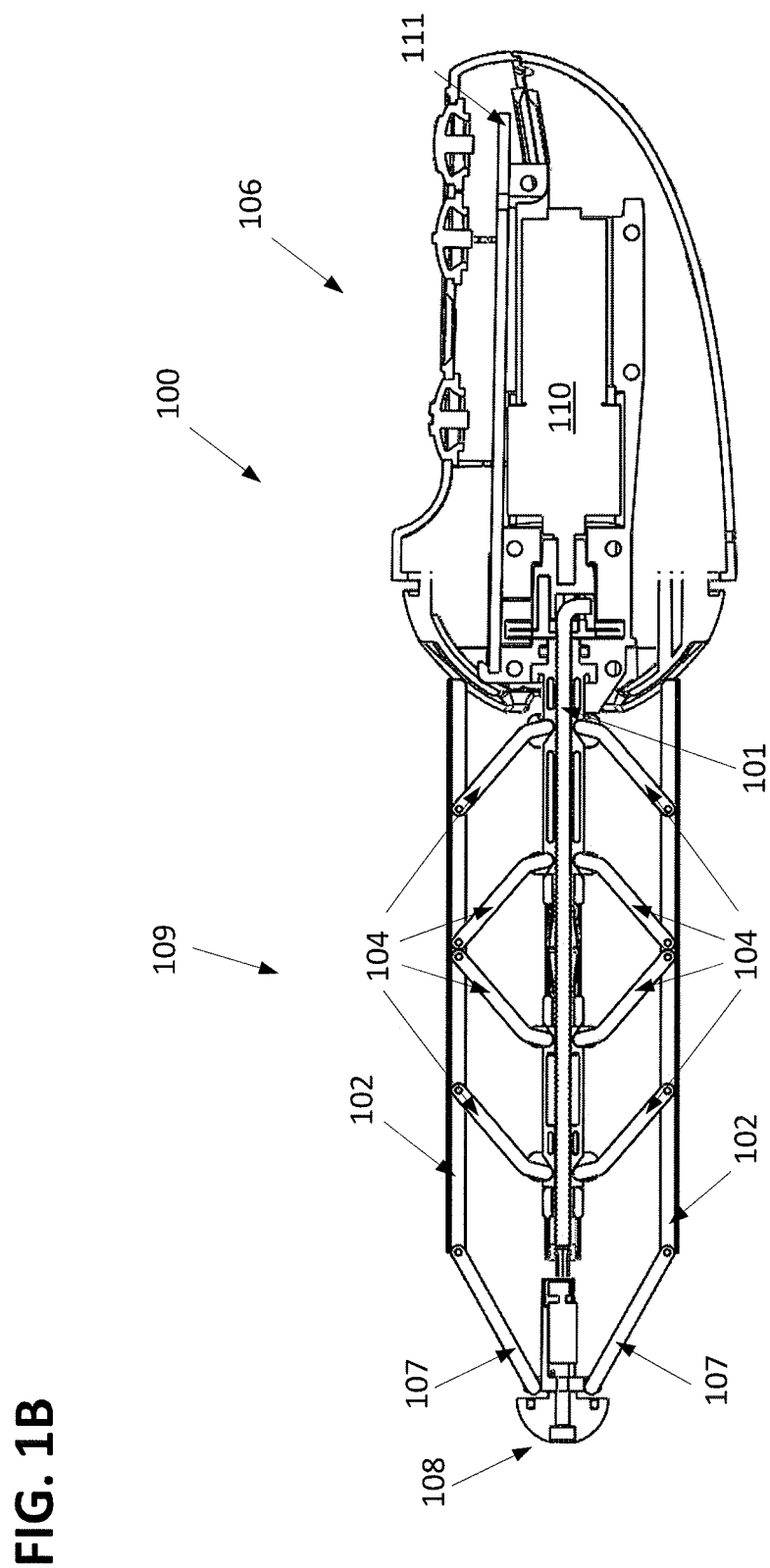

FIG. 1B shows a cross-sectional view of the vaginal dilation device 100 of FIG. 1A, but in the expanded configuration. Here it can be seen that the spines 102 and arms 104 have been expanded radially outwards from the central rod 101 of the device. It can also be seen that the spines expand to be generally parallel with each other and with the central rod 101. The distal arms 107 also expand slightly outwards from the central rod 101 and provide a rigid slope between the distal tip 108 and the expanded spines 102.

FIG. 1A shows the vaginal dilation device 100 in closed or compact configuration. When the device is in the closed configuration of FIG. 1A, spines 102 can be configured to rest near or against each adjacent spine so as to reduce the outer diameter of the device. In some embodiments, the diameter of the device (e.g., the distance between opposing spines) can be approximately 1.5 cm. In other embodiments, the spines do not rest against adjacent spines in the closed configuration, but this can result in the minimum outer diameter of the spines being larger, or alternatively, in the individual spines 102 having a smaller surface area, which may lead to patient discomfort during tissue dilation.

FIG. 1B shows the vaginal dilation device 100 in an open or expanded configuration. In the expanded configuration, the spines expand parallel to each other and to the central rod out to a maximum diameter of expansion. In some embodiments, this maximum diameter of expansion (e.g., the distance between opposing spines) is approximately 4 cm. In this expanded configuration, the diameter of the device at the distal tip 108 remains constant. In one embodiment, the diameter of the distal tip is 1.5 cm, which can be the same as the diameter of the device in the closed or compact configuration. The distal arms provide a slope or ramp between the distal tip and the spines when the device is in the expanded configuration. Thus, the diameter of the device where the distal arms meets the distal tip is the same as the diameter of the distal tip, and the diameter of the device where the distal arms meets the spines is the same as the distance between opposing spines.

As the device dilates to the expanded configuration, as shown in FIG. 1B, spines 102 and arms 104 of the device move radially outwards from the central rod, causing the spines to separate from one another. In some embodiments, the maximum diameter of the device can be approximately 4 cm in diameter in the expanded or dilated configuration. As can be seen from FIGS. 1A-1C, the distal tip maintains a constant profile or diameter between the closed and expanded configurations, i.e., the shape/profile and/or the diameter of the distal tip of the shaft portion does not change when the device is expanded. Furthermore, the distal arms provide a ramp or slop between the distal tip and the expanded spines.

Figure 1C:
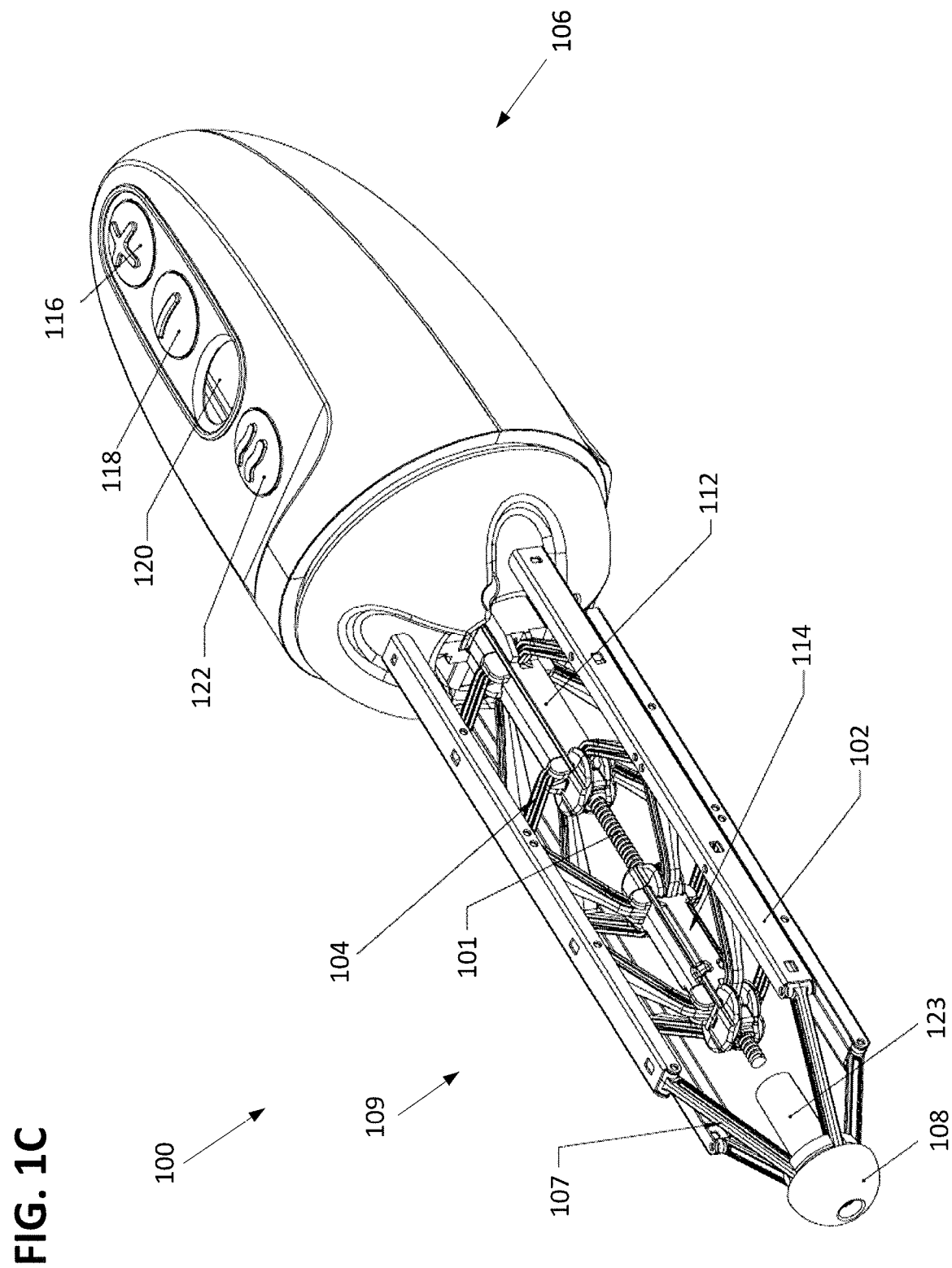

FIG. 1C is a perspective view of the vaginal dilation device 100 which further illustrates how the device expands from the closed configuration to the expanded configuration. As described above, the device 100 can include central rod 101, spines 102, arms 104, handle or frame 106, distal arms 107, distal tip 108, and a motor (not shown) that rotates the central rod to expand the arms and spines. FIG. 1C also shows buttons 116 and 118 which can be used to control expansion and contraction of the device. A diameter gauge 120 displays the diameter of the device (e.g., the distance between opposing spines). Button 122 can be used to activate a vibration feature of the device. In one embodiment, the device includes a vibrating element 123 disposed on or near the distal tip 108.

The diameter gauge 120 can be coupled to one or more sensors on or in the device, such as diameter sensors. In one embodiment, the diameter sensor is a rotary encoder that converts the rotary motion or rotation of the shaft into an analog or digital code that can be used the controller to determine the diameter of the shaft portion of the device. In the embodiment of FIG. 1C, the diameter gauge 120 is disposed on handle or frame 106, however the gauge can be disposed in any location on the device, or even remotely from the device such as on a display monitor. In some embodiments, the diameter gauge can be configured to indicate a diameter of the shaft portion of the device. A user can then refer the gauge to know the exact amount of tissue dilation. Diameter gauge 120 can comprise a simple binary readout or can have a scale showing the actual diameter of the device.

In some embodiments, the diameter of the shaft portion of the device can be recorded and stored by the controller of the device. This information can later be reviewed to reveal dilation history and progress. Recording the diameter can allow a user to track the exact diameter achieved, the timing between expansion, etc.

FIG. 1C further illustrates proximal hub 112 and mid hub 114. The arms 104 can each have one end connected via pins to the spine 102 and the other end connected to either the proximal hub or mid hub, depending on their location along the central rod. The proximal hub can be fixed relative to the motor, and can be attached directly to a distal end of the frame or handle 106. An interior of the mid hub can be threaded so as to engage corresponding threads of the central rod 101. When the motor is operated in the expansion direction it rotates the central rod, which engages the threads inside of the mid hub to draw the mid hub towards the proximal hub. As the mid hub is drawn towards the proximal hub, the angle of the arms relative to the central rod increases. The arms "stand up" as the mid hub moves proximally, thereby lifting the spines away from the central rod of the device. The spines 102 remain parallel to each other and to the central rod because there are multiple sets of arms per spine spaced along the length of the spine. The distal arms 107 connect the spines 102 to the distal tip 108. As the device expands, the angle between the distal arms 107 and the central rod also expands. The distal arms comprise a rigid material and provide a ramp or slope between the distal tip 108 and the spines.

When the vaginal dilation device is collapsed, partially expanded, or fully expanded, as shown in FIGS. 1A-1C, the shaft portion of the device comprises three distinct zones or regions: 1) the distal tip region, 2) the spine region, and 3) the distal arm region. Each of these regions comprises distinct diameter profiles and serves a unique purpose during the treatment of vaginismus.

The distal tip region comprises the length along the shaft portion defined by the distal tip 108. The distal tip region maintains a constant diameter profile, regardless of whether the device is collapsed, partially expanded, or fully expanded. The distal tip region provides a narrow constant tip profile that aids in insertion of the device into the vagina during treatment, regardless of if the device is in the smallest diameter (collapsed) configuration or the fully/partially expanded configuration.

The spine region comprises the length along the shaft portion defined by the spines 102, and represents the largest region of the device. As described above, the spines expand substantially parallel to each other and to the central rod 101. The diameter at a proximal end of the spine region (near the handle) will be substantially the same as the diameter at a distal end of the spine region (near where the spines join with the distal arms 107). As described above, the diameter gauge 120 displays the diameter of the device in the spine region (e.g., the distance between opposing spines). Therefore, the spine region is generally tubular in shape and provides a circular, expandable diameter profile that is defined by the user according to the desired diameter. The spine region of the vaginal dilation device provides dilation therapy to the vaginal canal, allowing the user to slowly become comfortable with increased diameters as described above to treat vaginismus.

Lastly, the distal arm region comprises the length along the shaft portion defined by the distal arms 107, between the distal tip 108 and the spines 102. When the vaginal dilation device is in the collapsed configuration, the distal arms can lay flat within the device, parallel to the central rod (as seen in FIG. 1A), and as the device expands, the distal arms gradually "ramp up" to form an angular support between the distal tip and the spines. The distal arm region is generally conical in shape and provides a circular diameter profile that ramps up from the diameter of the distal tip 108 (at the distal end of the distal arms) to the diameter between opposing spines (at the proximal end of the distal arms). The gradual increase in diameter along the distal arms from the distal tip to the spines allows the user to easily maneuver and reinsert the device during treatment as the patient feels comfortable.

In the embodiment of FIGS. 1A-1C, the vaginal dilation device 100 includes four spines 102 and four sets of four arms 104, totaling sixteen arms. It can be seen from FIG. 1C that two sets of arms connect the proximal hub to each of the spines, and two sets of arms connect the mid hub to each of the spines. In other embodiments, any number of spines and arms can be used. For example, one embodiment comprises as few as two or three sets of spines and arms, and other embodiments can include more than four sets of spines and arms, such as 5, 6, 7, or even 8 or more sets of spines and arms. The sets of spines and arms can be arranged symmetrically or asymmetrically around a central rod of the device.

The tissue contacting spines 102 and distal arms 107 can be designed to maintain stability through all dilation diameters. The spines, distal arms, and arms can comprise a rigid material such as stainless steel, aluminum, hard molded plastic, or the like. The spines and distal arms can be overmolded with a very compliant biocompatible elastomeric material to help evenly distribute force against the tissue and prevent trauma.

Referring still to FIGS. 1A-1C, the vaginal dilation device 100 can include an electronic controller 111 coupled to the motor within the device and configured to manually or automatically dilate, expand, and contract the spines and arms of the device. The electronic controller can be a printed circuit board (PCB) and can be disposed inside the handle or frame 106 of the device. The expansion and contraction of the device can be either manually or automatically controlled by a user by manipulating input device 110, e.g., pushing buttons 116 and 118. In some embodiments, the expansion of the device can be controlled in increments by manipulating the buttons. For example, referring to FIG. 1C, button 116 can be used to increase a diameter of the device button 118 can be used to decrease a diameter of the device. In some embodiments, the diameter of the device can be adjusted in increments (e.g., 1 mm increments with every press of the button).

Although most embodiments described herein show the arms as a scissor-like assembly, it should be understood that other methods and apparatus for expanding the spines can be used. For example, the arms can be singular arms attached to the spines (e.g., similar to a speculum).

The vaginal dilation device can be sized, shaped, and configured to penetrate approximately the first third, or 10-12 cm, of the vagina, and to gradually expand the vaginal introitus from a resting diameter of approximately 1.5 cm to a dilated diameter of approximately 4 cm. In some embodiments, the shaft portion of the vaginal dilation device can include guide markers to see how far the device has been inserted into the anatomy. The vaginal dilation device 100 can be configured to expand from a compact, closed configuration, as shown in FIG. 1A, to an expanded configuration, as shown in FIG. 1B. When the device is in the closed configuration, the spines can be seamlessly closed against each adjacent spine so as to form a solid shape (e.g., circle, oval, etc).

In some embodiments, the electronic controller of the vaginal dilation device can track and store information relating to the frequency of use of the device, and the amount and duration of which the device was expanded. The vaginal dilation device can collect this data and offer a report of how the user has been using the device, which can be further used by the user or a physician to determine optimal treatment protocols for that specific user.

Figure 2A:
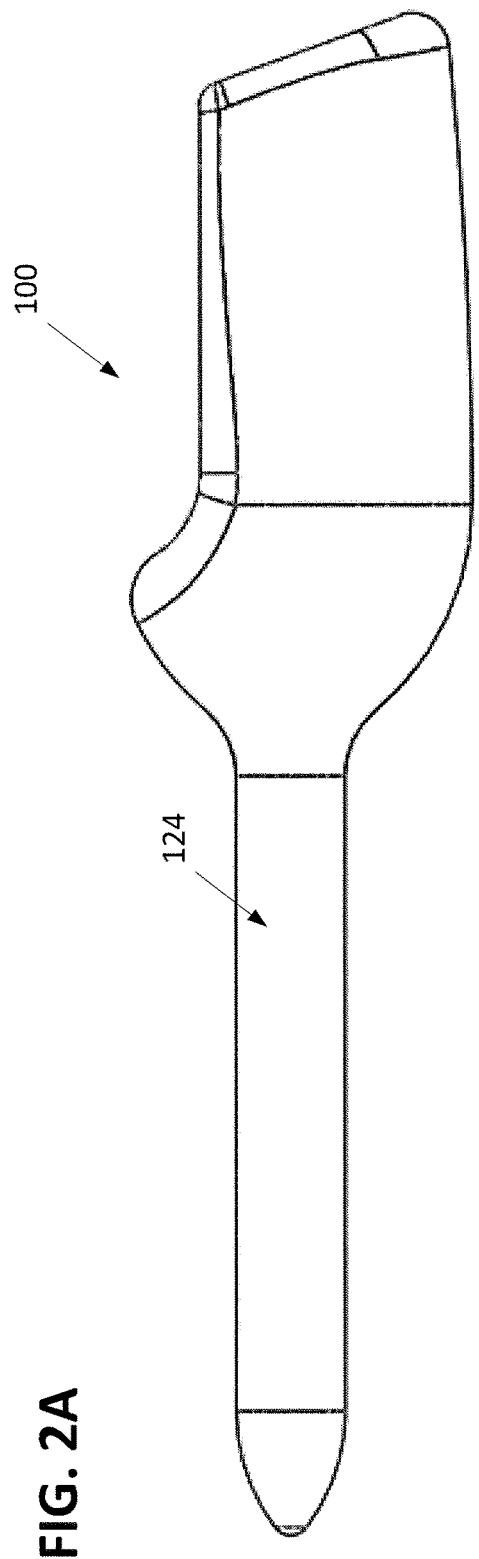
FIGS. 2A-2B show one embodiment of a sheath covering a vaginal dilation device.
Figure 2B:
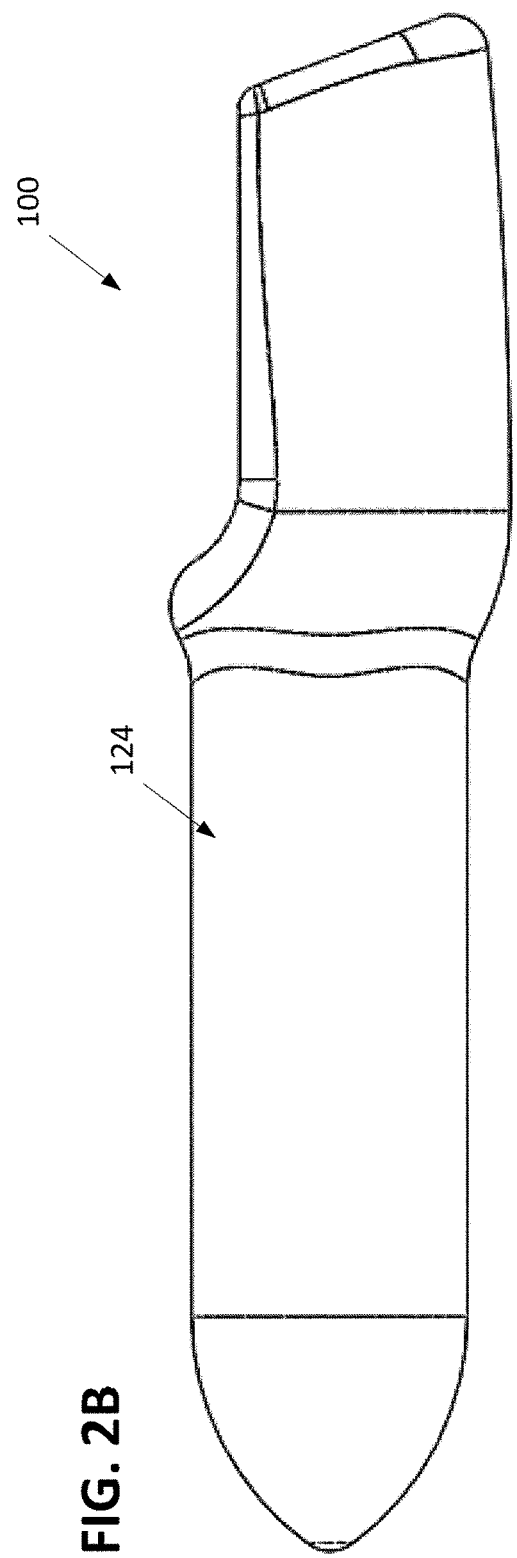

FIGS. 2A-2B show one embodiment of the vaginal dilation device 100 covered with a protective sheath 124, which creates an expandable sterile barrier to prevent infection and protect the moveable parts of the device from bodily fluids. The protective sheath can be an elastic material, such as latex, silicon, etc. In some embodiments, the sheath could also be made from a non-elastic material that is folded in and around the device, and unfolds as the device is expanded. FIG. 2A shows the vaginal dilation device in the closed or compact configuration, and FIG. 2B shows the vaginal dilation device in the expanded configuration.

Methods of using a vaginal dilation device will now be described. The vaginal dilation device can be inserted into the vagina of a patient. The device can include sensors for measuring a diameter of the device. After insertion, the device can be expanded by the user. In some embodiments, the user can control the expansion of the device by expanding the device incrementally (e.g., 1 mm per button press, 10 mm per button press, 0.5 cm per button press, 1 cm per button press, etc.). In some embodiments, the increment of expansion can be customized by the user to be any increment between 1 mm to 1 cm. As the device is expanded within the vagina, a diameter gauge of the device can give an indication of the diameter of the device (e.g., the distance between opposing spines) to indicate how far the vaginal tissue has dilated. The device can be used frequently by the patient to stretch and relax the pelvic muscles to treat vaginismus.

The vaginal dilation device of the present disclosure advantageously allows the user to expand the device while it is already inserted into the vaginal canal, avoiding the intimidating and painful large jumps in diameter between dilator sizes in traditional dilator kits. The user can expand the device in small increments, at their control, as they feel comfortable, which can lead to progressing through their treatment more quickly by expanding the device to larger diameters more quickly while doing so slowly at their control.

As the user becomes comfortable with the diameter, they can also manipulate the device within their vaginal canal, and in and out of the anatomy. This manipulation of the device in the anatomy can help the user become more comfortable with the size of the device. After manipulation, the user can also become more comfortable to increase the device diameter. The distal arms that "ramp up" between the distal tip and the spines allow the user to easily maneuver and reinsert the device as the patient feels comfortable. Additionally, the diameter readout gives the patient clear feedback of their treatment progress and gives the patients very clear goals and targets for their treatment It should be understood that these values are merely explanatory, as every woman's body and tissue response to treatment may be different. In general, however, a method of dilating vaginal tissue can comprise inserting a vaginal dilation device into the vagina, measuring a force applied by the vaginal dilation device to the vagina or measuring a diameter of the device, and dilating the vagina with the vaginal dilation device. In some embodiments, the device can be pre-programmed with optimal treatment protocols, where the device would automatically expand for the patient based on force or diameter for treating the user's specific vaginismus. In other embodiments, the user can manually determine their own optimal expansion program.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A vaginal dilation device adapted to expand from a collapsed configuration to an expanded configuration, comprising:
    a handle portion;
    a distal tip;
    a shaft portion extending distally from the handle portion to the distal tip and being sized and configured to contact vaginal tissue, the shaft portion comprising:
        a spine region extending distally from the handle portion, the spine region comprising a plurality of spines arranged parallel to each other, the spine region being generally tubular in shape and being configured to expand in diameter as the shaft portion expands from the collapsed configuration to the expanded configuration; and a distal arm region extending distally from the spine region to the distal tip of the vaginal dilation device, the distal arm region comprising a plurality of distal arms that connect the distal tip of the vaginal dilation device to a distal end of each of the plurality of spines, the distal arm region being generally conical in shape and being configured to provide a gradual increase in diameter along the shaft portion from the distal tip to the spine region wherein the distal tip of the vaginal dilation device is configured to maintain a constant diameter profile in both the collapsed configuration and the expanded configuration.

2. The device of claim 1 further comprising a diameter sensor configured to measure a diameter of the spine region.

3. The device of claim 2, further comprising a diameter gauge configured to display the diameter of the spine region to a user of the device.

4. The device of claim 1 further comprising a central rod that extends along a length of the shaft portion into the handle portion.

5. The device of claim 4 further comprising a motor coupled to the central rod, wherein operation of the motor causes the shaft portion to expand from the collapsed configuration into the expanded configuration.

6. The device of claim 5, further comprising a first hub and a second hub, the first hub being fixed relative to the motor, and the second hub being configured to move along the central rod when the motor is operated to expand the spine region and distal arm region.

7. The device of claim 6, comprising a plurality of arms that connect the first hub to the plurality of spines, and further comprising a plurality of arms that connect the second hub to the plurality of spines.

8. The device of claim 1 wherein a diameter of the spine region in the collapsed configuration is less than 1.5 cm.

9. The device of claim 1, wherein a diameter of the spine region in the expanded configuration is approximately 2-4 cm.

10. The device of claim 1, further comprising an expansion button disposed on the handle portion, the expansion button being configured to incrementally increase a diameter of the spine region when actuated by a user of the device.

11. The device of claim 10, wherein the diameter is incrementally increased by 1 mm with each actuation of the expansion button.

12. The device of claim 10, wherein the diameter is incrementally increased by less than 1 cm with each actuation of the expansion button.

13. The device of claim 1, further comprising a vibrating element disposed in the shaft portion.

* * * * *